United States Patent [19]

Edamura et al.

[11] 3,966,937

[45] June 29, 1976

[54] METHOD FOR PROTECTING PLANTS FROM SOIL-BORNE PLANT DISEASE ORGANISMS USING METHYL-(4-METHYLPHENYL)-SUB-STITUTED-TETRAZOLO (1,5-a)-PYRIMIDINES

[75] Inventors: Fred Y. Edamura, Concord; Ronald J. Sbragia, Clayton, both of Calif.

[73] Assignee: The Dow Chemical Company, Midland, Mich.

[22] Filed: Jan. 20, 1975

[21] Appl. No.: 542,481

Related U.S. Application Data

[62] Division of Ser. No. 451,668, March 14, 1974, Pat. No. 3,920,654.

[52] U.S. Cl. .......................... 424/251; 424/DIG. 8
[51] Int. Cl.² ........................................ A01N 9/22

[58] Field of Search .................... 424/251, DIG. 8

[56] References Cited
UNITED STATES PATENTS

| | | | |
|---|---|---|---|
| 3,776,911 | 12/1973 | Stacey | 424/251 |
| 3,835,137 | 9/1974 | Wagner | 424/251 |

OTHER PUBLICATIONS

Bulow, Ber. vol. 42 (1909), pp. 4429–4438.

*Primary Examiner*—V. D. Turner
*Attorney, Agent, or Firm*—S. Prestonn Jones; Gary D. Street; C. Kenneth Bjork

[57] ABSTRACT

Methyl-(4-methylphenyl)-substituted-tetrazolo-(1,5-a)pyrimidine and methods employing the same for the systemic protection of plants from soil-borne plant disease organisms.

8 Claims, No Drawings

3,966,937

METHOD FOR PROTECTING PLANTS FROM SOIL-BORNE PLANT DISEASE ORGANISMS USING METHYL-(4-METHYLPHENYL)-SUBSTITUTED-TETRAZOLO (1,5-A)-PYRIMIDINES

CROSS REFERENCE TO RELATED APPLICATION

This is a division of application Ser. No. 451,668, filed Mar. 14, 1974, now U.S. Pat. No. 3,920,654, issued Nov. 18, 1975.

BACKGROUND OF THE INVENTION

The present invention relates to a novel methyl-(4-methylphenyl)-substituted-tetrazolo(1,5-a)pyrimidime compound, compositions containing the same and methods utilizing the same in systemically protecting plants from attack by soil-borne plant disease organisms.

The related prior art discloses 5-methyl-7-phenyltetrazolol(1,5-a)pyrimidine, Ber. 42, 4429 (1909). No systemic plant protectant activity for such compound has been reported and the compound of the present invention has not been previously described. The systemic plant protectant utility of the claimed compound is unexpected and surprising since such compound has little or no direct contact, i.e., in vitro, activity against soil-borne plant disease organisms. Moreover, it has been found that the claimed compound is superior in plant protectant activity to the above-mentioned prior art compound, which also demonstrates phytotoxicity to plants, at dosage rates necessary to give extended protection.

SUMMARY OF THE INVENTION

The invention relates to a novel methyl-(4-methylphenyl)-substituted-tetrazolol(1,5-a)pyrimidine compound (hereinafter referred to as the "active ingredient") of the formula:

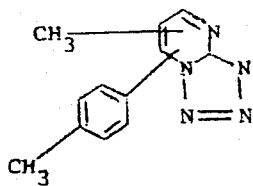

wherein the methyl group is in the 5 (or 7)-position and the 4-methylphenyl group is in the 7 (or 5)-position. While infrared and nuclear magnetic resonance spectra support the above structure and physical data indicate the presence of a pure compound, rather than an isomeric mixture, the exact point of substitution of the respective methyl- and 4-methylphenyl groups has not been resolved. It has been found that the application of an effective amount of the active ingredient to plant life forms or their soil environment systemically protects the plant life forms against soil-borne plant disease organisms.

In general, the compound of the present invention is prepared by mixing p-methylacetophenone with sodium metal and ethyl acetate to form a reaction mixture containing a first intermediate believed to be the sodium salt of 1-(4-methylphenyl)-1,3-butanedione. The p-methylacetophenone, usually about 2 molar proportions thereof, is added portionwise over a period of about one hour to a solution of the sodium metal, about 2 molar proportions, and ethylacetate. The reaction mixture temperature is maintained below about 40°C. during the addition and, following the completion of the addition, the reaction mixture is maintained at ambient temperatures with stirring for a period of from 1 to about 16 hours. A 5-aminotetrazole monohydrate reactant, about 2 molar proportions, and a suitable carrier medium, such as ethanol, propanol or the like, are added to the reaction mixture and the resulting mixture is heated at reflux temperatures for a period of from about 2 to about 6 hours to form a second intermediate thought to be methyl-, 4-methylphenyl-substituted 4,5-dihydrotetrazole(1,5-a)pyrimidin-5-ol. The second intermediate is recovered, the procedures hereinafter being referred to as "recovering", by subsequently cooling and filtering the reaction mixture and washing the solids removed with a suitable solvent, such as one of the carrier mediums hereinabove mentioned, and combining the filtrate with the reaction mixture. The reaction mixture is concentrated by evaporation to give a pasty residue which is slurried with benzene, the slurry filtered, and the solids removed washed with benzene. The filtrates are combined and concentrated by evaporation to yield the second intermediate as a pale yellow crystalline solid. The second intermediate is dissolved in a suitable carrier medium and acidified with a concentrated acid, e.g., concentrated hydrochloric, sulfuric, and the like, to dehydrate the intermediate and form the product of the above formula. The concentrated acid is usually added dropwise over a period of about 30 minutes while maintaining the reaction mixture temperature below about 30°C. Following acidification, the reaction mixture can be slowly mixed with water to precipitate the product from the reaction mixture if desired. The product thus obtained can be further purified by washing with additional quantities of water and a suitable solvent as above mentioned. The product can also be recrystallized from a suitable solvent, such as acetone or the like.

In the present specification and claims, the term "plant" or "plant life form" is employed to designate all parts of a plant and includes seeds, seedlings, tuber, cutting, the root system, hereinafter commonly referred to as root, the crown, stalk, stem, foliage or leaf system, fruit or flower. As used herein, the terms "systemic" or "plant protectant" activity by an active ingredient refers to the assimilation and translocation of the chemical from the site of application into and through the vascular system of the plant whence it is distributed throughout the plant tissues, particularly in the underground portions of plants. Obviously, this is a complex process which is unpredictable, and is encountered much more infrequently than superficial or contact activity. Thus, if the active ingredient is applied to seeds, accumulation of the active compound is principally found in the underground system of the germinating seed; if applied to the above ground portions of the plant life form or to the environment thereof, e.g., soil, the active ingredient generally translocates and principally accumulates in the underground portion of the plant.

Representative soil-borne plant disease organisms which are known to attack the below ground portion of plants include Verticillium, Rhizoctonia, Phytophthora, Pythium and Thielaviopsis. Of these, water mold disease organisms such as Pythium and Phytophthora are believed to be the principal disease problems for desirable plants; the active ingredients employed herein are particularly effective against Phytophthora. The present invention thus is useful in providing for the control of the various soil-borne diseases which are known to attack a variety of plants, such as, for example, cereal crops, such as, corn, wheat, barley, rice and sorghum; truck crops, such as, cucurbits (melons, cucumbers, squash, etc.), crucifiers (cabbage, broccoli, etc.), tomatoes and peppers; legumes, such as, peanuts, soybeans, beans, peas, and alfalfa; other crops, such as, tobacco, potatoes, cotton, sugar beets and pineapple; perennial crops, particularly in the seedling stage, such as, citrus (orange, lemon, grapefruit, etc.), apples, pears, peaches, cherries, nut crops (walnuts, pecans, almonds, etc.), grapes, avocado; non-food grass species commonly referred to as turf and nursery and ornamental crops, such as, chrysanthemums, azaleas, rhododendrons, violets, carnations, lilies and shade and foliage ornamentals, such as, philodendrons, Schefflera and Dieffenbachia and the like and gymnosperms such as pine, Arborvitae, spruce, junipers and the like.

Plant-protecting amounts of an active ingredient is conveniently applied to plants and/or plant envirnoment, e.g., soil, either before or after the plant has been attacked by soil-borne plant disease organisms, by procedures such as soil injection, drenching with an aqueous composition, seed treatment, topical spraying, furrow spraying or other techniques known to those skilled in the art. The only limitation upon the mode of application employed, is that it must be one which will place the toxicant in direct contact with seeds or plant parts.

The exact dosage of the active ingredient employed will vary depending upon the specific plant, hardiness of the plant, nature of the soil and mode of application. Generally, for practical applications on a commercial scale, the active ingredient can be broadly applied at application rates of from about 0.1 to about 5.0 pounds or more on a per acre basis. Amounts of various diluted solutions containing the active ingredient in terms of parts per million (ppm) necessary to achieve a desired application rate can readily be determined by those skilled in the art given the active ingredient concentration. For example, the application of 200 gallons of a solution containing 600 ppm active ingredient is generally equivalent to the application of about one pound of active ingredient per acre. A preferred range is from about ¼ to about 3.0 or more pounds per acre. Commercially, seed treatments are customarily recommended on the basis of ounces per hundredweight per bushel. This can be expressed in ppm as from about 5.0 to about 1000 ppm or more. The upper limit in any of the foregoing application rates is, of course, determined by phytotoxic manifestations encountered by the treatment, which will depend upon the compound employed and the various factors set forth above. Of course, lesser or greater rates can be utilized depending upon the particular situation.

Larger amounts of the active ingredient advantageously may be applied when treatments are employed which distribute the material throughout the soil. For example, when the active ingredient is applied as an at-plant row treatment or as an early season post-plant side-dress treatment, those amounts of chemical not proximal to plant roots are essentially unavailable to the plant and therefore not effective as set forth hereinabove. In such practices, amounts of the active ingredient need to be increased to rates as high as about 10 pounds or more per acre to assure the requisite effective quantity of active ingredient is made available to the plants.

The present invention can be carried out by employing the active ingredients directly, either singly or in combination. However, the present invention also embraces the employment of liquids, dusts, wettable powders, granules or encapsulated compositions containing at least one of said compounds as active ingredient. In such usage, the compound or compounds can be modified with one or more of a plurality of inert solid or liquid carrier adjuvants including inert solvents, inert liquid carriers and/or surface active dispersing agents and coarsely or finely divided inert solids. The augmented compositions are also adapted to be employed as concentrates and subsequently diluted with additional inert carrier to produce other compositions in the form of dusts, sprays, granules, washes or drenches. In compositions where the adjuvant is a coarsely or finely divided solid, a surface active agent or the combination of a surface active agent and a liquid additament, the adjuvant cooperates with the active component so as to facilitate the invention. Whether the composition is employed in liquid, wettable powder, dust, granule or encapsulated form, the active compound will normally be present in an amount of from about 2 to 98 percent by weight of the total composition.

In the preparation of dust, or wettable powder compositions, the active ingredient can be compounded with any of the finely divided solids, such as pyrophyllite, talc, chalk, gypsum, fuller's earth, bentonite, attapulgite, starch, casein, gluten and the like. In such operations, the finely divided carrier is ground or mixed with the toxicant or wet with a solution of the active ingredient in a volatile organic solvent. Also, such compositions when employed as concentrates can be dispersed in water, with or without the aid of dispersing agents to form spray mixtures.

Granular formulations are usually prepared by impregnating a solution of the active ingredient in a volatile organic solvent onto a bed of coarsely divided attapulgite, bentonite, diatomite, or the like.

Similarly, the active ingredient can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable inert organic liquids which can be employed in the compositions include petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active ingredient.

In addition, other liquid compositions containing the desired amount of active ingredient can be prepared by dissolving the same in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400°F. at atmospheric pressure and having a flash point above 80°C. The proportion of the compounds of this invention employed in a suitable solvent may vary from about 2 to about 50 percent or higher.

A preferred liquid composition includes the use of the active ingredient or ingredients in combination with surface active dispersant agents only. In such compositions, it is preferred to use ionic and non-ionic blends of such dispersant agents in combination with one or more of the active materials. A particular advantage of such a formulation is that phytotoxicity associated with certain inert solvents, such as, xylene, methylene chloride, and like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments and the like.

Water miscible organic solvents such as lower alcohols or propylene glycol can be added to depress the freezing point and further cooperate with the above system in that they are essentially non-phytotoxic.

Description of the Preferred Embodiments

In order that the present invention may be more fully understood, the following examples are provided to illustrate the manner by which it can be practiced but, as such should not be construed as limitations upon the overall scope of the same.

EXAMPLE 1

Methyl-(4-methylphenyl)-substituted-tetrazolo(1,5-a)-pyrimidine p-Methylacetophenone (286 grams; 2.0 moles) was added portionwise over a period of about 1 hour to a stirred suspension of sodium (47.8 grams; 2.00 moles) in ethyl acetate (480 grams) under nitrogen, with a cooling bath to maintain the reaction mixture temperature below about 40°C. Following the completion of the p-methylacetophenone addition, the resulting pasty reaction mixture was stirred for a period of about 16 hours at ambient temperatures. 5-Aminotetrazole monohydrate (206 grams; 2.0 moles) and ethanol (600 milliliters) were added to the reaction mixture containing what is believed to be the sodium salt of a 1-(4-methylphenyl-1,3-butanedione intermediate, and the resulting mixture was heated at reflux temperatures for a period of about 4 hours. Following the reaction period, the reaction mixture was cooled, filtered, and the solid material removed by filtration and washed with 300 ml of ethanol. The reaction mixture, also containing the 300 ml ethanol filtrate, was concentrated in vacuo and the pasty residue obtained triturated with one liter of benzene. The resulting slurry was filtered, the solids washed with another liter of benzene, and filtrates combined and concentrated in vacuo to give 260 grams of a pale yellow solid product, believed to be a methyl-, 4-methylphenyl-substituted 4,5-dihydrotetrazolo-(1,5-a)pyrimidin-5-ol intermediate. This solid yellow intermediate was dissolved in 1300 ml of ethanol and concentrated hydrochloric acid (150 ml) was added dropwise to said solution over a period of about 30 minutes while maintaining the reaction mixture temperature below about 30°C. After another 30 minute period, an additional 3 liters of water was slowly added to the reaction mixture. The resulting product precipitate was recovered by filtration and washed successively with 3 liters of water and then with 200 ml of ethanol. The product thus obtained was recrystallized from acetone. As a result of such operations, a 5(or 7)-methyl-7(or 5)-(4-methylphenyl)-tetrazolo(1,5-a)pyrimidine compound having a melting point of 198°–199.5°C. was recovered as a white crystalline solid. Infrared and nuclear magnetic resonance spectra were consistent with the proposed structure. Elemental analysis calculated for $C_{12}H_{11}N_5$ (percent): C, 63.99; H, 4.92; N, 31.09. Found (percent): C, 63.83; H, 5.14; N, 30.81.

EXAMPLE 2

Separate treating compositions containing the 5(or 7)-methyl-7 or 5)-(4-methylphenyl)tetrazolo(1,5-a)pyrimidine test compound (A) and the prior art 5-methyl-7-phenyltetrazolo(1,5-a)pyrimidine compound (B) at concentrations of 1600 and 400 ppm. Six inch pots were filled with soil infested with *Phytophthora parasitica* var. *nicotianae* and a transplanting hole approximately 3 inches in diameter and about 2 inches deep was made in each pot. Various groups of pots were then treated by pouring 100 ml of treating composition into the transplant hole; immediately after such treatment, a tobacco seedling with at least two leaves 3–4 inches long was transplanted into each pot. The treated pots, along with untreated control pots, were left undisturbed for 2 days and then watered; all pots were maintained under conditions condusive to good growth. The untreated control plants died about five days following the beginning of the tests and the test pots were observed after 15 days and thereafter until the test compound failed to give complete control of the disease organism. The results are set forth in the following table:

TABLE I

| Compound | App'l Rate ppm | Days of Disease Control Following Treatment |
| --- | --- | --- |
| A. | 1600 | *54 |
|  | 400 | 36 |
| B. | 1600 | **21 |
|  | 400 | **15 |

*Test terminated but complete disease inhibition was still being obtained at such time.
**Plants displayed phytotoxic symptoms.

The foregoing data establish the superior activity of the claimed compound as a systemic plant protectant agent for extended periods of time over the related prior art compound. The phytotoxicity of the prior art compound was also observed at lower application rates.

While several particular embodiments of this invention are shown above, it will be understood, of course, that the invention is not to be limited thereto, since many modifications may be made, and it is contemplated, therefore, by the appended claims, to cover any such modifications as fall within the true spirit and scope of this invention.

We claim:

1. A composition useful for systemically protecting plants from diseases caused by soil-borne plant disease organisms comprising from about 2 to 98 percent by weight of the total composition of a methyl-(4-methylphenyl)-substituted tetrazolo(1,5-a)pyrimidine compound having the general formula:

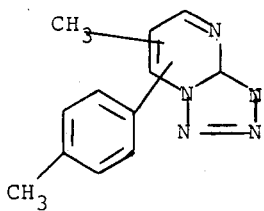

wherein the methyl substituent is in the 5(or 7)- position and the 4-methylphenyl substituent is in the 7(or 5)- position, in combination with an inert solid or liquid carrier therefor, the said compound being the product of a process comprising the steps of (1) forming a reaction mixture containing a sodium 1-(4-methylphenyl)-1,3-butanedione intermediate by the reaction of about two molar proportions of each of p-methylacetophenone and sodium metal in the presence of ethylacetate, said reaction being carried out at a temperature below about 40°C, (2) reacting said reaction mixture of step (1) with about 2 molar proportions of 5-aminotetrazole monohydrate in the presence of a carrier medium under reflux conditions for from about 2 to about 6 hours to form a reaction mixture containing a methyl-(4-methylphenyl)-substituted 4,5-dihydrotetrazole(1,5-a)pyrimidin-5-ol intermediate, (3) recovering said intermediate formed in step (2), (4) dissolving the intermediate recovered in step (3) in a suitable carrier medium, and (5) treating said intermediate solution of step (4) with a concentrated acid at a temperature below about 30°C, thereby dehydrating said intermediate to the methyl-(4-methylphenyl)-substituted tetrazolo(1,5-a)pyrimidine compound.

2. A method for systemically protecting plants from diseases caused by the soil-borne plant disease organisms Verticillum, Rhizoctonia, Phytophthora, Pythium and Thielaviopsis which comprises applying to said plants or their environment, a plant protecting amount of a methyl-(4-methylphenyl)-substituted tetrazolo(1,5-a)pyrimidine compound having the general formula:

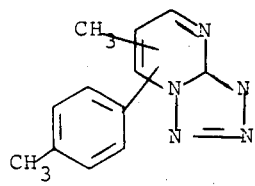

wherein the methyl substituent is in the 5(or 7)- position and the 4-methylphenyl substituent is in the 7(or 5)- position, the said compound being the product of a process comprising the steps of (1) forming a reaction mixture containing a sodium 1-(4-methylphenyl)-1,3-butanedione intermediate by the reaction of about two molar proportions of each of p-methylacetophenone and sodium metal in the presence of ethylacetate, said reaction being carried out at a temperature below about 40°C, (2) reacting said reaction mixture of step (1) with about 2 molar proportions of 5-aminotetrazole monohydrate in the presence of a carrier medium under reflux conditions for from about 2 to about 6 hours to form a reaction mixture containing a methyl-(4-methylphenyl)-substituted 4,5-dihydrotetrazolo(1,5-a)pyrimidin-5-ol intermediate, (3) recovering said intermediate formed in step (2), (4) dissolving the intermediate recovered in step (3) in a suitable carrier medium, and (5) treating said intermediate solution of step (4) with a concentrated acid at a temperature below about 30°C, thereby dehydrating said intermediate to the methyl-(4-methylphenyl)-substituted tetrazolo(1,5-a)pyrimidine compound.

3. The method as defined in claim 2 wherein the plants are contacted with said plant protectant prior to their being attacked by said plant disease organisms.

4. The method as defined in claim 2 wherein the plants are contacted with said plant protectant after being attacked by said plant disease organisms.

5. The method as defined in claim 2 wherein the plant protectant is applied to the environment.

6. The method as defined in claim 2 wherein plant seeds are contacted with said plant protectant.

7. The method as defined in claim 2 wherein said plant protectant is employed in combination with an inert carrier.

8. The method of claim 2 wherein said plant protectant is employed at a rate of from about 0.1 to about 5.0 pounds per acre.

* * * * *